Figure 1:
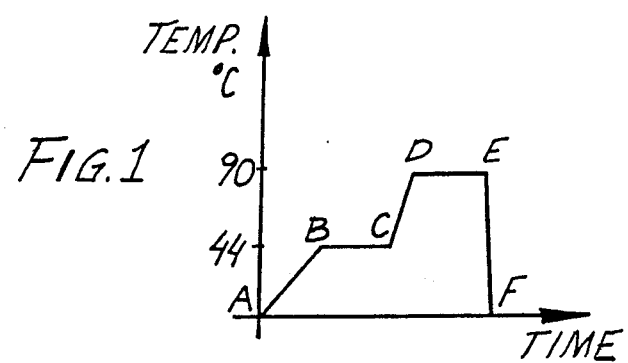

United States Patent [19]

Ericsson et al.

[11] Patent Number: 4,900,819
[45] Date of Patent: Feb. 13, 1990

[54] METHOD IN THE PRODUCTION OF CRYSTALLINE EXPLOSIVES

[75] Inventors: Per Ericsson, Kungsängen; Leif Svensson, Karlshamn; Nils-Ingvar Olsson, Uppsala; Bertil Bergström, Degerfors, all of Sweden

[73] Assignee: Nobel Kemi AB, Karlskoga, Sweden

[21] Appl. No.: 184,131

[22] Filed: Apr. 21, 1988

[30] Foreign Application Priority Data

Apr. 22, 1987 [SE] Sweden ............................ 8701644
Apr. 22, 1987 [SE] Sweden ............................ 8701643

[51] Int. Cl.$^4$ .................. C07D 251/06; C07D 257/02
[52] U.S. Cl. ...................................... 540/475; 544/251
[58] Field of Search ...................... 540/475; 544/251

[56] References Cited

U.S. PATENT DOCUMENTS

| | | | |
|---|---|---|---|
| 4,086,228 | 4/1978 | Solomon et al. ................... | 260/239 |
| 4,638,065 | 1/1987 | Svensson et al. ................... | 540/475 |
| 4,767,854 | 8/1988 | Lewicki .............................. | 540/475 |
| 4,785,094 | 11/1988 | Levinthal .......................... | 540/475 |

FOREIGN PATENT DOCUMENTS

| | | | |
|---|---|---|---|
| 590851 | 1/1960 | Canada ............................... | 540/475 |
| 47-14112 | 4/1972 | Japan ................................. | 540/475 |
| 615419 | 1/1949 | United Kingdom ................ | 540/475 |

*Primary Examiner*—David B. Springer
*Attorney, Agent, or Firm*—Pollock, Vande Sande & Priddy

[57] ABSTRACT

The disclosure relates to a method of initiating a crystal growth prior to filtering off, from the mother liquor in which they were produced, of such crystalline explosives of the type hexogen and octogen produced by the so-called Bachmann process or variations of this process.

According to the invention, the mother liquor is, after the end of the chemical reaction proper, subjected to a pressure-heat treatment which initiates the partial dissolution of the crystalline explosives obtained in the process, giving rise, after cooling of the mother liquor, to larger crystals which may more readily be filtered off.

According to a further improvement of the invention a relatively pure octogen may be extracted from the mother liquor by way of a thermo-filtering of said liquor at a temperature of 60°–110° C.

12 Claims, 1 Drawing Sheet

METHOD IN THE PRODUCTION OF CRYSTALLINE EXPLOSIVES

TECHNICAL FIELD

The present invention relates to a method of extracting crystalline explosives of the type octogen and hexogen from the acetic acid acidic mother liquor in which they were produced by nitration of hexamethylene tetramine (hexamine) with ammonium nitrate, acetic acid anhydride, acetic acid and nitric acid.

A further improvement of the invention relates to a method of directly extracting in crystalline form, relatively pure octogen from the mother liquor.

The above-outlined process for the industrial production of both octogen, or octahydro-1,3,5,7-tetranitro-1,3,5,7-tetrazocine, normally abbreviated to HMX, and hexogen or hexahydro-1,3,5-trinitro-1,3,5-triazine, also entitled cyclonite and normally abbreviated to RDX, generally goes under the title of the

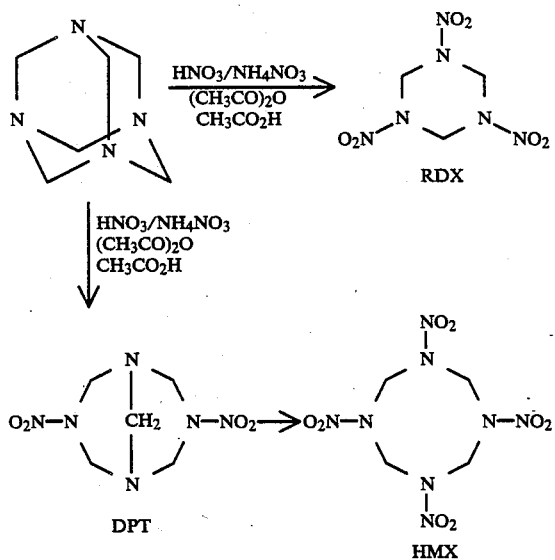

Bachmann process. According to the simplified formula presented below, this process gives both octogen and hexogen and a number of nitrated byproducts.

The obtained amounts of octogen and hexogen, respectively, may vary somewhat, like the total yield, depending upon how the process is put into practice. However, this is of no importance in the present context and will not, therefore, be discussed in greater detail here. On the other hand, it is essential to ascertain that the state-of-the-art technique only makes it possible to extract the obtained octogen and hexagen, respectively, from the mother liquor in the form of extremely fine particulate crystals which can be separated from the mother liquor at but low capacity and which show a marked propensity for blocking the filters.

According to the state-of-the-art technology, the crystalline product filtered off from the mother liquor after completed reaction consists of a fine crystalline mixture of octogen and hexogen, in which the octogen substantially consists of the undesirable, more sensitive $\alpha$ octogen modification which must be recrystallized with a suitable solvent into the less sensitive $\beta$ octogen variant, at the same time as it is also desirable to split up the obtained crystalline product into relatively pure octogen and hexogen fractions, respectively. The recrystallization of the octogen is effected today using a suitable solvent.

OBJECT OF THE PRESENT INVENTION

The present invention has for its object to propose an improved method for extracting octogen and hexogen from the acetic acid acidic mother liquor after a completed Bachmann process or closely related process. The method according to the present invention gives rise to considerably larger octogen and hexogen crystals, respectively, than in prior art processes. This larger crystal size is an invaluable advantage in that it facilitates and hastens the filtering off of the crystals from the mother liquor. By such means, the filtering time may be reduced considerably, at best down to a third as compared with smaller crystals obtained according to prior art techniques, and; at the same time, the risk of blockage of the filters is correspondingly reduced. The larger crystals obtained according to the present invention are not only more easily filtered, they also have a considerably smaller total surface and can, therefore, bond with comparably smaller amounts of acetic acid on their surface which, in its turn, entails a correspondingly reduced contamination of washing liquids and recrystallization agents.

According to the Bachmann process, the nitration reaction between the included components hexamine, ammonium nitrate, acetic acid anhydride and nitric acid is carried out in an acetic acid acidic solution at a temperature dependent upon the reaction conditions and normally lying between approximately 44° C. and approximately 65° C. for hexogen. When the reaction has been completed, water has been added as a matter of routine, and the temperature has been raised to the close proximity of the boiling temperature of the mother liquor, or about 90° C., this temperature level being maintained for approximately half an hour for hydrolyzation of certain unstable, undesirable byproducts which, in such instance, are broken down, the reaction mixture being thereafter cooled to room temperature, there being then obtained the previously mentioned extremely fine crystalline - and consequently sparingly filterable fraction which normally has consisted of 85-90% octogen and 10-15% hexogen.

The most manifest drawbacks inherent in this process are, as have previously been pointed out, the fine crystalline structure and consequential problems in filtering-off and washing and the high amount of hexogen.

According to the present invention, it has now become possible to realize a marked crystal growth by a combined pressure and temperature treatment of the reaction mixture after completion of the nitration reaction but before the filtering-off of the obtained crystals. Hence, in the method according to the present invention, the nitration reaction proper and the subsequent water addition are carried out in accordance with prior art methodology. Thereafter, the temperature of the reaction mixture is raised, under elevated pressure, to a temperature which is markedly above the boiling point of the mother liquor, this temperature being maintained at elevated level for degradation of the previously mentioned unstable byproducts, in which event the already formed octogen and hexogen crystals also partly convert into solution. Thereafter, the temperature is once again reduced with a reformation and crystal growth as a result, whereafter the thus obtained crystals may be filtered off from the mother liquor.

We have further been able to ascertain that the elevated temperature characteristic of the present invention may not exceed 200° C. and should lie under 170° C., since excessively high temperatures have proved to result in a partial degradation of formed products and a consequential deterioration in yield. However, a certain reduction in the yield may be accepted against the background of the manifest advantages afforded by the larger crystals. As an example, mention might be made of the fact that the temperature increase to 170° C. for two hours gave a weight loss of approximately 50% for octogen, while a temperature increase to 160° C. for the same period of time gave a weight loss of approximately 80% for hexogen, which, in both cases, must be considered as excessively high losses, even taking into account the advantages gained by the obtained larger crystals and the consequentially simplified filtering of these crystals from the mother liquor. On the other hand, temperature increases of 110°-130° C. for a maximum of two hours may prove to give rise to clearly acceptable weight losses of both octogen and hexogen. The primary purpose of the previously mentioned pressure increase characteristic of the method according to the present invention is to permit a temperature increase above the boiling temperature of the mother liquor. As a rule, no active measure need be adopted for raising the pressure, it being fully sufficient to carry out the temperature increase in an autoclave of other closed vessel which, automatically, will then give the desired pressure increase. Practical tests have, moreover, demonstrated that there is no reason to allow the pressure to exceed 5 bar. Furthermore, it may be appropriate to reduce the pressure to atmospheric before the obtained crystals are filtered off, since it is then possible to carry out a fully normal filtering process.

The pressure increase which takes place on heating of both hexogen and octogen in a closed vessel or autoclave derives from a temperature-initiated disintegration of, primarily, residual and byproducs of the type linear nitroamines such as AcAn (1,9-diacetoxy-2,4,6,8-tetranitro-2,4,6,8-tetrazanonane). Moreover, the desired end product - primarily when this consists of hexogen - can be decomposed to a certain degree if the temperature becomes excessively high. The reason for this is that hexogen, because of its less favorable molecular bonding angles, is not as stable as octogen.

We have now also surprisingly found that the above-mentioned method may be further improved so that it is possible to obtain directly a first extremely pure octogen fraction instead of the previously obtained mixture of octogen and hexogen crystals. According to the present invention, this result will be achieved if the temperature, after the above-described pressure-heat treatment is first lowered to a temperature slightly below the boiling point of the mother liquor, i.e., approximately 90° C., where the reaction mixture is thermo-filtered. We have, namely, found that already at that stage there are formed such large amounts of readily filterable crystals that filtering may be carried out without difficulty. It has further proved that such a thermofiltering gives a crystal fraction whose hexogen content is as low as 0,1-3% while the residual amount consists substantially of α octogen.

Hence, a recrystallization of the octogen cannot be avoided, but the obtained octogen fraction will, as is apparent from the foregoing, be unusually pure and free of hexogen.

The thermo-filtering must be executed at a temperature which should not lie markedly above 90° C., since too much octogen will then convert into solution with a low yield as a result, nor below 60° C. since hexogen will then begin to deposit in large amounts and wil reduce the purity of the octogen fraction.

After this thermo-filtering, the mother liquor is cooled to room temperature and there filtered a second time, there being obtained a raw product which has proved to consist of approximately 50% octogen and 50 % hexogen.

The method according to the present invention will now be described further in conjunction with the appended Figures and Examples. However, the present invention should not be considered as restricted to these Examples, being defined in the appended claims.

Referring to the Drawings, FIGS. 1-4 show, in simplified form and not to scale, method diagrams for the production and extraction of octogen and hexogen.

Figure 2:
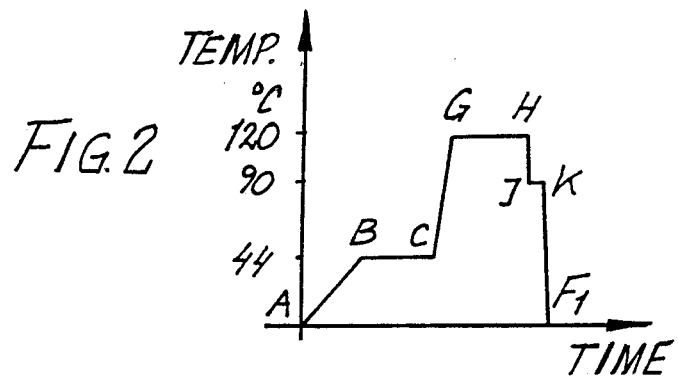
Figure 3:
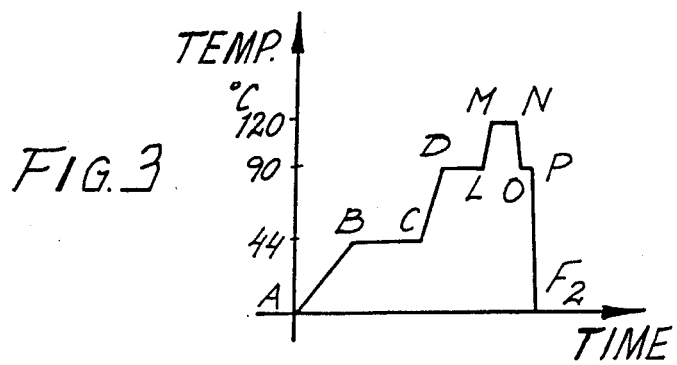

FIG. 1 illustrats the prior art technique, while FIGS. 2 and 3 show two variations of the method according to the present invention including as well the pressure-heat treatment as the thermo-filtering.

Figure 4:
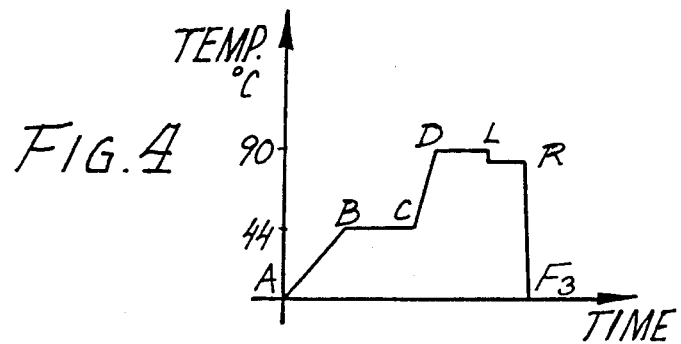

FIG. 4 illustrates yet a further variation of the method according to which the pressure-heat treatment is excluded.

In FIGS. 1-4, steps A-C are common to all. Steps A-B mark the admixture of hexamine, ammonium nitrate, acetic acid anhydride and nitric acid to the acetic acid acidic initial solution, while steps B-C mark the nitration reaction which is carried out at a temperature of approximately 44° C. dependent upon the reaction conditions. At point C, the reaction is completed and water is added. Thereafter, the prior art technique and the method according to the present invention differ.

According to the state-of-the art (FIG. 1) the temperature of the reaction mixture is raised after the addition of water at point C to between approximately 90° C. and the boiling point of the reaction mixture and is kept there for approximately ½ to 1 hour (points D-E) in order thereafter to be cooled to room temperature and filtered at F.

According to the first variation of the method according to the present invention illustrated in FIG. 2, the temperature of the reaction mixture is raised, after the water addition at C in a closed vessel under pressure generated thereat (which, for reasons of safety and yield, is allowed to rise to a maximum of approximately 5 bar), to a temperature of 110°-130° C. and is kept at this level between G and H for ½ to 2 hours, whereafter the temperature is reduced to approximately 90° C. at I, whereupon the mixutre is de-aired and thermo-filtered between I and K. The heat treatment is required for degradation of unstable residual products and the high temperature results in a partial dissolution of the already formed octogen and hexogen crystals, which results in larger crystals when the reaction mixture is cooled once again.

Finally, the temperature is lowered to room temperature and the reaction mixture is filtered a second time at $F_1$.

According to this method, there will, as mentioned above, be obtained an extremely pure octogen fraction at the first filtering stage between I and K, and a mixture of octogen and hexogen at the second filtering stage $F_1$.

According to the second variation of the method according to the present invention illustrated in FIG. 3, the reaction mixture is heated between C and D to approximately 90° C., is held at that level for ½-2 hours between D and L for degradation of unstable products, whereafter the temperature, once again under elevated pressure (max 5 bar)in a closed vessel between L and M, is raised to 110°-130° C., is held at that level for less than 2 hours between M and N in order, between N and O, to be cooled to 90° C., de-aired and, between O and P, thermo-filtered a first time for extracting ocotogen, whereafter the temperature of the reaction mixture is lowered to room temperature and the reaction mixture is filtered a second time at $F_2$ for extracting the residual amounts of ocotogen and hexogen.

According to the variation illustrated in FIG. 4, the reaction mixture is heated, between C and D, to approximately 90° C., is kept at that level for ½ to 2 hours between D and L for degradation of unstable by-products, whereafter the temperature of the reaction mixture is adjusted to the desired filtering temperature, 60°-90° C. The mixture is filtered a first time between L and R for extracting octogen. Thereafter, the temperature of the reaction mixture is lowered to room temperature and the reaction mixture is filtered a second time at $F_2$ for extracting residual amounts of octogen and hexogen.

EXAMPLE 1 (The pressure heat treatment)

The following experiment was carried out to provide empirical support for the crystal growth which the heat treatment according to the present invention initiates in a raw hexogen. As an expression of the obtained crystal growth, use was made of the filtration time applicable to each individual sample in one and the same filtration apparatus. This consisted of a filter funnel with a diameter of 9.5 cm in which each sample after completed filtration gave a filter cake of a thickness of a approximately 20 mm. Each sample consisted of 120 g of dried raw hexogen and 400 ml mother liquor. The employed hexogen had been produced by a conventional Bachmann process of the above-described type. The mother liquor was taken from the same process. The Table below indicates, for each sample, the time and temperature for the pressure-heat treatment according to the present invention, as well as the acutal filtration time in the above-indicated apparatus. The reference sample was filtered after 1 hour's continuous agitation at room temperature. All heat treatment according to the invention was carried out in one-liter autoclaves in which the pressure for the pressure-heat treated raw hexogen never exceeded 5.5 atmospheres and as a rule was rapidly stabilized at approximately 4 atmospheres.

TABLE

| Sample | Treatment temp (°C.) | Treatment time (min) | Filtration time (sec) |
|---|---|---|---|
| RDX ref | — | — | 202 |
| RDX 1 | 120 | 60 | 52 |
| RDX 2 | 120 | 30 | 115 |
| RDX 3 | 120 | 30 | 114 |
| RDX 4 | 120 | 60 | 77 |
| RDX 5 | 110 | 60 | 104 |
| RDX 6 | 110 | 60 | 109 |
| RDX extreme | 160 | 120 | (x) |

(x) In the extreme experiment with raw hexogen, the pressure in the autoclave rose to 55 atmospheres because of considerable disintegration which, in its turn, resulted in the fact that only a sixth of the original hexogen amount could be recovered.

EXAMPLE 2 (The pressure heat treatment)

The effect of the heat treatment on octogen (HMX) is apparent from the experiment series presented below. In each experiment, 20 g of raw octogen was employed dissolved in 340 ml of mother liquor from the octogen production. On this occasion, the filtration was effected in a filter funnel of a diameter of 7 cm. Otherwise, the same technique was employed as in Example 1.

The relevant facts are apparent from the Table below, as will be apparent from the Table, which also includes disclosures on the pressure, this pressure is lower than average of 4 atmospheres which applies to the hexogen experiments according to Example 1. This is probably because of the slight tendency of octogen to auto-decomposition.

TABLE 2

| Sample | Treatment temp (°C.) | Treatment time (min) | Pressure (atmospheres) | Filtration time (sec) |
|---|---|---|---|---|
| HMX 1 | 120 | 60 | 1.8-2.2 | 0.33 |
| HMX 2 | 110 | 60 | 1.3-1.5 | 0.50 |
| HMX 3 | 120 | 5 | 1.8 | 0.53 |
| HMX 4 | 120 | 60 | 1.8-2.2 | 0.32 |
| HMX ref | 90 | 60 | 0 | 1.43 |

All values in the Table are mean values after a plurality of identical experiments.

EXAMPLE 3 (The thermo-filtering)

A conventional octogen synthesis according to Bachmann was carried out with a starting amount of hexamine of 14 g. When the addition of the reactants was complete and the reaction mixture had been allowed to after-react for 2 hours, 50 ml of water was added and the temperature was raised to 90° C., being held at that level for 30 min. Thereafter, the reaction mixture was filtered at the same temperature, 90° C., and washed with water.

The mother liquor was cooled and filtered. In the HMX fraction, filtered off at 90° C., there was obtained 22 g of a product which contained 0.2% hexogen and the remainder octogen.

In the RDX fraction, filtered off at room temperature, there was obtained 8.9 g of a product which contained 48% octogen and 52% hexogen.

EXAMPLE 4 (The thermo-filtering)

Example 1 was repeated up to and including the water addition. Thereafter, the temperature was raised to 120° C. and held at that level for 60 min., the pressure rising at the same time to 2.4 atmospheres. Thereafter, the temperature was lowered to 90° C. and the pressure reduced to atmospheric. The reaction mixture was filtered and the product was washed with water. The mother liquor was cooled and filtered once again.

In the HMX fraction, filtered off at 90° C., there was obtained 21.5 g of a product which contained 0.3% hexogen and the remainder octogen.

In the RDX fraction, filtered off at room temperature, there was obtained 8.4 g of a product which contained 48% octogen and 52% hexogen.

We claim:

1. A method of extracting octogen and hexogen crystalline explosives from the acetic acid acidic mother liquor in which they were produced by nitration of hexamine with ammonium nitrate, acetic acid anhydride and nitric acid, characterized in that the mother liquor with said crystalline explosives formed in the reaction and deposited therein is, after the end of the reaction but before the filtering-off of said explosives, heated in a closed vessel to a temperature in excess of 90° C. but less than 200° C. at a pressure of maximum of 5 bar and is held at said pressure and temperature for a period of time of at least 15 minutes but not exceeding 2 hours, whereafter the octogen and hexogen crystalline explosives are filtered off from the mother liquor.

2. The method as claimed in claim 1, characterized in that the mother liquor with said crystalline explosives deposited therein is heated in a closed vessel to a temperature which does not exceed 170° C.

3. The method as claimed in claim 1, characterized in that the temperature and pressure of the mixture are reduced from the levels employed at said reaction after the end of the reaction and before the said crystalline explosives are filtered off from the mother liquor.

4. The method as claimed in claim 3 characterized in that the temperature and pressure of the reaction mixture are reduced to a temperature of 60°–110° C. and normal atmospheric pressure respectively and that the explosive said crystalline explosives, almost entirely consisting of octogen, deposited thereat, are separated off from the mother liquor by thermo-filtering.

5. The method as claimed in claim 4, characterized in that the temperature of the mother liquor, after the thermo-filtering, is cooled to room temperature, and that the thus formed residual crystals of both octogen and hexogen are filtered off in a second filtering stage.

6. The method of claim 2, wherein said temperature is between 110° C. and 130° C.

7. The method as claimed in claim 6, characterized in that the temperature and pressure of the mixture are reduced from the levels employed at said reaction after the end of the reaction and before the said crystalline explosives are filtered off from the mother liquor.

8. The method as claimed in claim 2, characterized in that the temperature and pressure of the mixture are reduced from the levels employed at said reaction after the end of the reaction and before the said crystalline explosives are filtered off from the mother liquor.

9. The method as claimed in claim 8, characterized in that the temperature and pressure of the reaction mixture are reduced to a temperature of 60°–110° C. and normal atmospheric pressure, respectively, and that the said crystalline explosives, almost entirely consisting of octogen, disposed thereat, are separated off from the mother liquor by thermo-filtering.

10. The method as claimed in claim 7, characterized in that the temperature and pressure of the reaction mixture are reduced to a temperature of 60°–110° C. and normal atmospheric pressure, respectively, and that the said crystalline explosives, almost entirely consisting of octogen, deposited thereat, are separated off from the mother liquor by thermo-filtering.

11. The method as claimed in claim 10, characterized in that the temperature of the mother liquor, after the thermo-filtering, is cooled to room temperature, and that the thus formed residual crystals of both octogen and hexogen are filtered off in a second filtering stage.

12. The method as claimed in claim 9, characterized in that the temperature of the mother liquor, after the thermo-filtering, is cooled to room temperature, and that the thus formed residual crystals of both octogen and hexogen are filtered off in a second filtering stage.

* * * * *